United States Patent [19]
Schürch

[11] Patent Number: 5,383,017
[45] Date of Patent: Jan. 17, 1995

[54] APPARATUS AND METHOD FOR DETECTING CONTAMINANTS IN TEXTILE PRODUCTS INDEPENDENTLY OF THE DIAMETER OF THE TEXTILE PRODUCTS

[75] Inventor: Georg Schürch, Pfäffikon, Switzerland

[73] Assignee: Gebruder Loepfe AG, Kepten, Switzerland

[21] Appl. No.: 3,572

[22] Filed: Jan. 13, 1993

[30] Foreign Application Priority Data

Jan. 31, 1992 [CH] Switzerland ............... 284/92

[51] Int. Cl.$^6$ .............................................. G01B 9/02
[52] U.S. Cl. ...................................... 356/238; 356/430
[58] Field of Search ............... 356/238, 429, 430, 385; 250/562, 572

[56] References Cited

U.S. PATENT DOCUMENTS

| | | | |
|---|---|---|---|
| 4,389,575 | 6/1983 | Cole | 356/430 |
| 4,436,427 | 3/1984 | Schwartz | 356/238 |
| 4,739,176 | 4/1988 | Allen et al. | 356/430 |
| 4,812,043 | 3/1989 | Vanstaen | 356/429 |
| 4,963,757 | 10/1990 | Liefde et al. | 356/429 |
| 5,054,317 | 10/1991 | Laubscher | 356/238 |
| 5,182,457 | 1/1993 | Hagmann | 356/430 |

FOREIGN PATENT DOCUMENTS

| | | |
|---|---|---|
| 197763 | 10/1986 | European Pat. Off. |
| 674379A5 | 5/1990 | Switzerland |
| WO91/10898 | 7/1991 | WIPO |

*Primary Examiner*—Richard A. Rosenberger
*Assistant Examiner*—Russell C. Wolfe
*Attorney, Agent, or Firm*—Harness, Dickey & Pierce

[57] ABSTRACT

For the detection of the presence of contaminants in yarn a first optical sensor is used to measure the amount of light reflected from the yarn. The signal from this sensor not only depends on the presence of contaminants but also on the diameter of the yarn. For eliminating the dependence on the yarn's diameter, a second signal is recorded, which depends essentially only on the yarn's diameter. By appropriate combination of these two signals in a microprocessor system the influence of the yarn's diameter in the first signal can be eliminated.

13 Claims, 2 Drawing Sheets

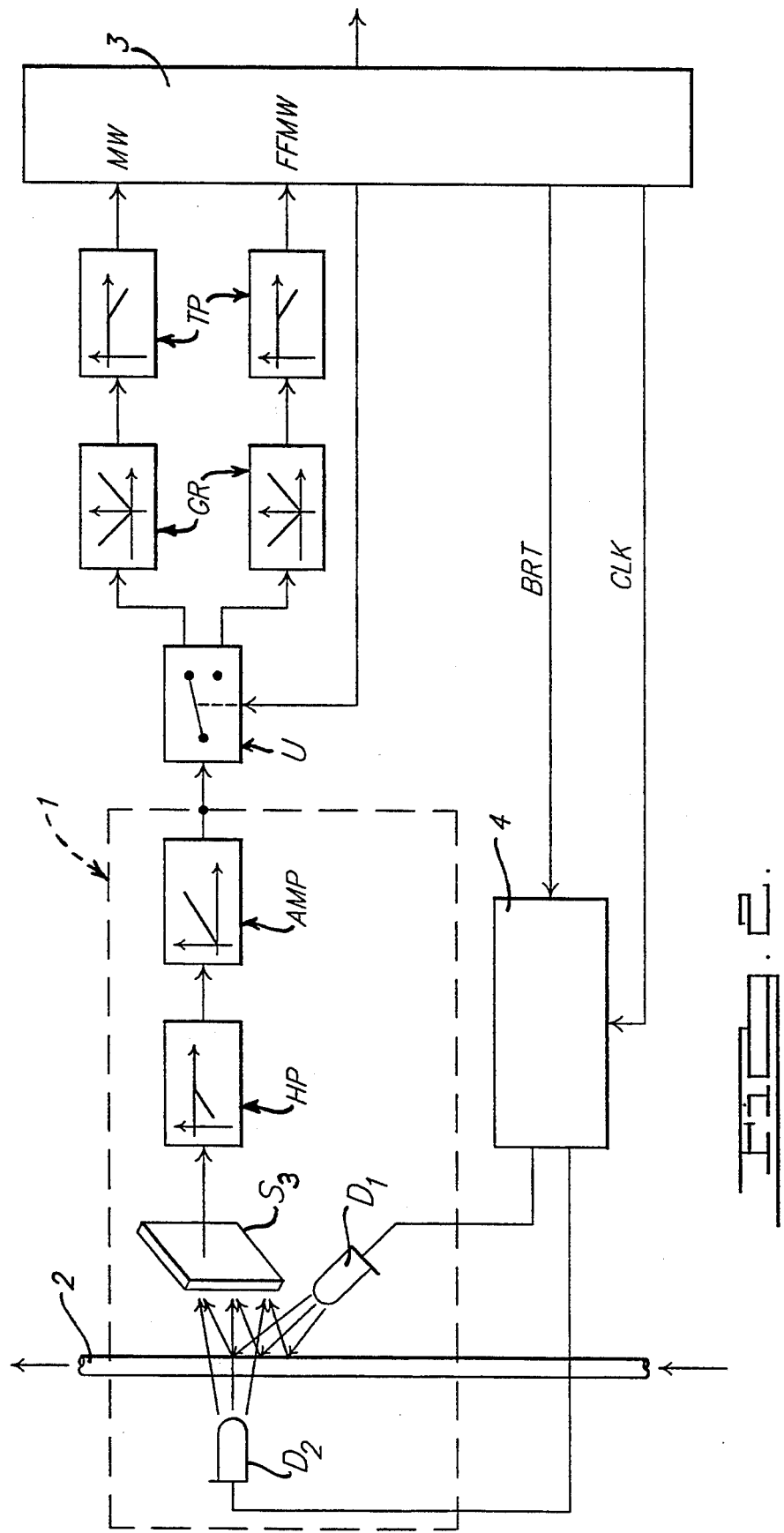

APPARATUS AND METHOD FOR DETECTING CONTAMINANTS IN TEXTILE PRODUCTS INDEPENDENTLY OF THE DIAMETER OF THE TEXTILE PRODUCTS

BACKGROUND OF THE INVENTION

1. Field of the Invention

The invention relates to a method and an apparatus for the detection of contaminants, especially foreign fibers, in an elongated textile product, such as a yarn or a thread.

Before spinning, raw fibers, e.g. cotton fibers, are mechanically cleaned by carding. In this way larger contaminants can be removed. Still, it cannot be ruled out that smaller contaminants, such as foreign fibers, remain in the yarn. These are spun into the yarn and can affect the following processing steps as well as the quality of the final product.

2. Description of the Prior Art

Presently, so-called yarn cleaners are used for controlling the diameter of the yarn and for removing sections of yarn with too large or too small a diameter.

Furthermore, devices have been developed for optically detecting contaminants and removing the corresponding sections of yarn. Such devices, as they are e.g. described in EP-0 197 763 or in CH-674 379, are essentially based on a detection of light reflected from the yarn. Devices based on this optical method recognize the contaminants because of their different optical properties.

However, such optical sensors measuring in reflection, transmission or projection usually generate signals that depend on the diameter of the yarn. Therefore, a basic problem in designing the above mentioned devices lies in generating a signal that is essentially independent of this diameter such that only signals caused by contaminants are detected. The resulting devices are therefore usually complicated and require a careful calibration for each type of yarn, and are difficult to obtain a signal from that is sufficiently independent of the yarn's thickness.

SUMMARY OF THE INVENTION

Hence, it is a general object of the present invention to provide a method and an apparatus for the detection of contaminants, especially foreign fibers, in a thread or yarn.

It is a further object of the invention to easily provide a signal that characterizes the presence of contaminants and is independent of the diameter of the thread or yarn.

In order to implement these and still further objects of the invention, which will become more apparent as the description proceeds, two results of separate measurements are combined such that a diameter (thickness) dependence of the first measurement is compensated by a diameter dependence of the second measurement.

For this purpose, a conventional yarn cleaner detector can be combined with a contamination detector. The yarn cleaner detector generates a signal proportional to the yarn's diameter. This signal is used to correct the signal generated by the contamination detector, such that the resulting signal is essentially independent of the yarn's diameter. Preferably, this correction is carried out in a microprocessor system.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 2 shows a corresponding diagram of a second embodiment of the invention.

DESCRIPTION OF A PREFERRED EMBODIMENT

Figure 1:
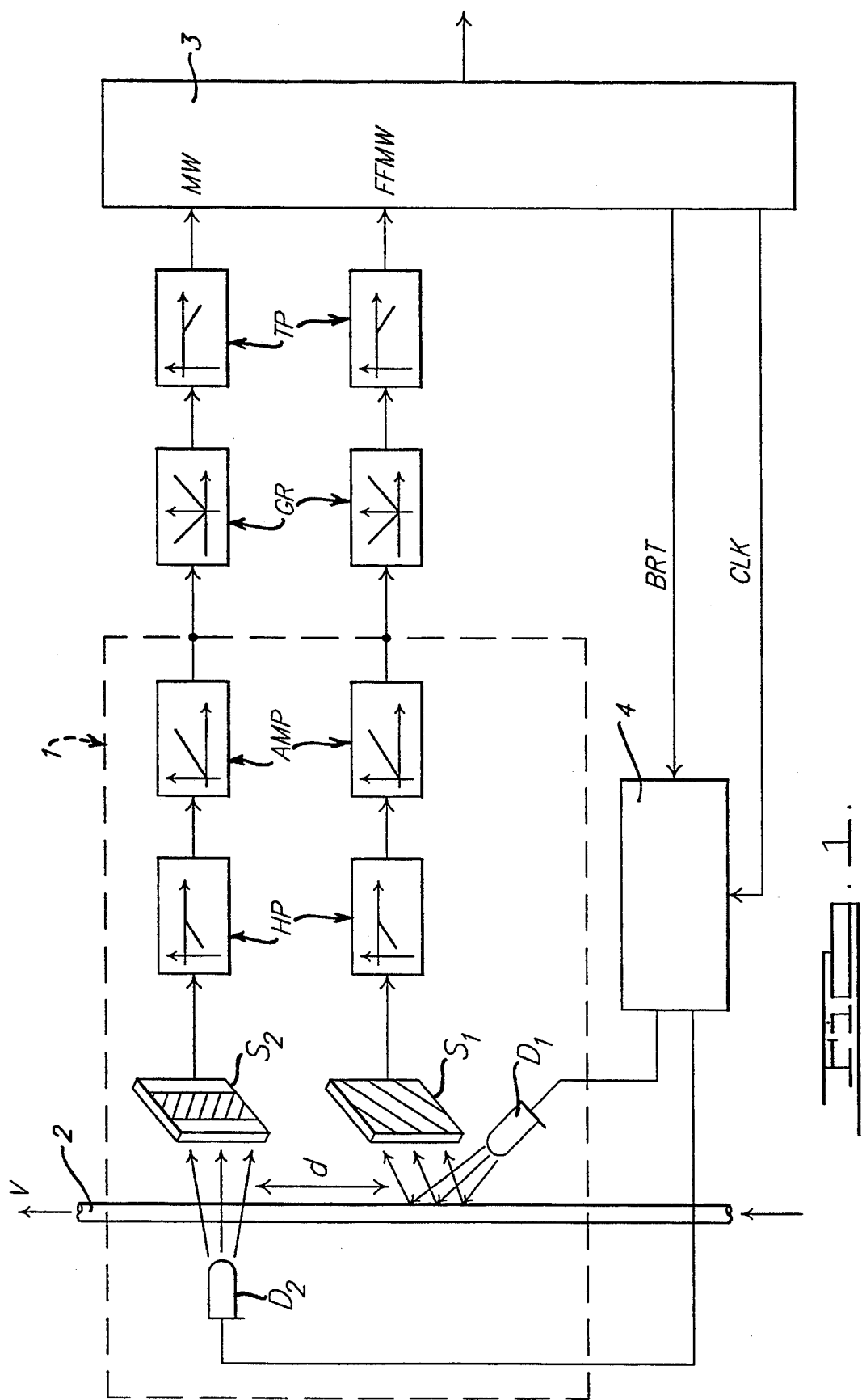
FIG. 1 shows a schematic diagram of a first embodiment of the invention.

A first embodiment of the apparatus is shown in FIG. 1. This apparatus comprises two locations of measurement, which are housed in one measuring head 1, through which the yarn is led. In the first location of measurement a detector $S_1$ is used for receiving pulsed light emitted from a source of light $D_1$ and reflected from the yarn. A change in the received quantity of light and/or a change in its spectral distribution indicates the presence of contaminations in the fiber. The received quantity of light is also dependant on the thickness of the yarn. For details on the design of corresponding detection systems we refer to EP-0 197 763 or CH-674 379. It should be noted, however, that most of the adjustment procedures described therein are not required here.

Preferably, a light emitting diode with a short wavelength, e.g. in the green, blue or ultraviolet spectral region, is used. At such wavelengths the contrast and the strength of the signal are improved.

The pulsed signal from the sensor $S_1$ is filtered in a high pass filter HP and amplified in an amplifier AMP, which are arranged in the measuring head 1. Then the signal is rectified in a rectifier GR and led through a low pass filter TP to generate the DC-signal FFMW (foreign fiber signal), which is then fed to a microprocessor system 3, where it is converted into a digital signal. Contaminants in the yarn as well as variations in the yarn's diameter are manifested as amplitude variations of this signal FFMW.

In a second location of measurement in the head 1 a signal is recorded that is proportional to the yarn's diameter. This signal is generated by illuminating a section of yarn by a pulsed light source $D_2$ and projecting its shadow image onto a detector $S_2$. This kind of projection for determining a yarn's thickness is known from conventional yarn cleaners and is therefore not described in detail. The resulting pulsed signal from the sensor is again led through a high pass filter HP and an amplifier AMP, which are located in the measuring head 1. Then the signal is rectified in the rectifier GR, filtered in a low pass filter TP and converted to a digital value for further processing in the microprocessor system 3. The resulting signal MW depends only on the yarn's thickness.

In the microprocessor system 3 corresponding values of the signals FFMW and MW are combined and evaluated. If the yarn is moving with a known speed v and if the distance d between the two locations of measurement is known, this can be carried out by combining delayed signals of the first location of measurement with the signals of the second location of measurement, wherein the delay T is given by T=d/v. The signals FFMW and MW are mathematically combined to a corrected value $FFMW_{KOMP}$ according to the formula $$FFMW_{KOMP} = K * FFMW / MW,$$

wherein K is a constant coefficient, FFMW is the signal derived from detector $S_1$, and MW is the signal derived from the detector $S_2$. $FFMW_{KOMP}$ is a corrected signal that does not depend on the yarn's diameter but varies in the presence of contaminations.

Other formulae for deriving a corrected value are possible, such as appropriate addition or subtraction of the signals.

The corrected signal $FFMW_{KOMP}$ can subsequently be processed by the microprocessor 3 for detecting the presence of contaminants and for controlling a yarn cleaner to remove such contaminants.

Furthermore, the microprocessor 3 is used for controlling the driver 4 of the pulsed light emitting diodes $D_1$ and $D_2$. For this purpose it generates a clock signal CLK as well as a signal BRT for controlling the brightness of the diodes.

As it has been mentioned above, the two locations of measurement are preferably arranged in sequence in a measuring head 1. It is, however, also possible to combine these two locations into one single location, as it is shown in FIG. 2. Instead of two sensors $S_1$ and $S_2$, one single sensor $S_3$ is used for recording light from the two alternatively pulsed light diodes $D_1$ and $D_2$. While one of these diodes is switched on, the other is switched off, and vice versa. Synchronously to the switching of these diodes, a switch U is actuated for separating the two signals after they have passed through the high pass filter HP and the amplifier AMP. The two separated signals are then rectified and filtered individually. Further processing and corrections of these signals are carried out with the methods described above. The microprocessor system 3 is used to drive the LED driver 4 and to synchronously actuate the switch U.

In the two embodiments described above, it is, of course, possible to replace the single light emitting diodes $D_1$ and $D_2$ by groups of several diodes, as it is e.g. described in EP-197 763.

If the measurement is carried out in two separate locations, as it was described in the first embodiment, in one of these locations the yarn's diameter is determined while in the other location a signal is measured that depends on contaminants in the yarn as well as on its diameter. If contaminations are to be detected not only on one side of the yarn but over its whole circumference, the yarn can e.g. be placed in a zone of measurement that is diffusely flooded by light. A contamination in the yarn will lead to a change of the amount of light reflected back from the yarn into the zone of measurement, thereby changing the brightness in this zone of measurement. This can be detected by an appropriately placed detector, as it is e.g. described in EP-0 197 763.

In all these embodiments the described mathematical combination of the two signals allows an easy elimination of the influence of the yarn's diameter in the resulting signal.

While there are shown and described present preferred embodiments of the invention, it is to be distinctly understood that the invention is not limited thereto, but may be otherwise variously embodied and practiced within the scope of the following claims.

I claim:

1. A method for the detection of contaminants in an elongated textile product, said method comprising
    a first measurement generating a first signal, the magnitude of said first signal depending on the presence of a contaminant in said textile product as well as on the diameter of said textile product, and
    a second measurement generating a second signal, the magnitude of said second signal only depending on the diameter of said textile product,
    wherein said first signal and said second signal are combined such that the dependence on the diameter of said textile product is eliminated in said first signal.

2. The method of claim 1, wherein said first measurement essentially comprises a detection of light being reflected by said textile product being illuminated, and wherein said second measurement essentially comprises an optical projection of said textile product being illuminated onto a light sensitive detector.

3. The method of claim 1, wherein said first and said second signal to be combined are derived essentially from a same part of said textile product.

4. The method of claim 1, wherein one of said first and second signals is measured in a first location of measurement while the other of said first and second signals is measured in a second location of measurement, wherein said first location of measurement is arranged at a distance from said second location of measurement, and wherein said textile product is led first through said first and then through said second location of measurement, and wherein the signal measured in said first location is delayed before being combined with the signal measured in said second location of measurement, such that said two signals being combined correspond essentially to a same part of said textile product.

5. The method of claim 1, wherein said first and said second signal are combined by dividing said first by said second signal.

6. The method of claim 2, wherein the light used in said first and said second measurement is pulsed and has a wavelength equal to or shorter than a wavelength of green light.

7. An apparatus for the detection of contaminants in an elongated textile product comprising at least one light sensitive detector, at least two sources of light and an evaluation circuit, wherein
    at least one of said sources of light is positioned to illuminate said textile product such that light reflected from said textile product is detected by said at least one detector to generate a first signal,
    at least one of said sources of light is positioned to illuminate said textile product such that a shadow of said textile product is projected onto said at least one detector to generate a second signal, and
    wherein said evaluation circuit comprises a calculator adapted to mathematically combine said first and said second signals for eliminating a contribution of the diameter of said textile product to said first signal.

8. The apparatus of claim 7 comprising a first light sensitive detector for receiving light reflected from said textile product and
    a second light sensitive detector, onto which detector said shadow of said textile product is projected.

9. The apparatus of claim 8, wherein said second detector is part of a yarn cleaner detector for monitoring the diameter of said textile product.

10. The apparatus of claim 7, wherein said evaluation circuit comprises a calculator adapted to mathematically combine said first and said second signal for eliminating a contribution of the diameter of said textile product to said first signal.

11. The apparatus of claim 7, wherein at least the sources of light generating light to be reflected from said textile product are light emitting diodes with a wavelength equal to or shorter than a wavelength of green light.

12. An apparatus for the detection of contaminants in an elongated textile product comprising:
at least one light sensitive detector;
at least two sources of light;
at least one of said sources of light being positioned to illuminate said textile product such that light reflected from said textile product is detected by said at least one detector to generate a first signal,
at least one of said sources of light being positioned to illuminate said textile product such that a shadow of said textile product is projected onto said at least one detector to generate a second signal, and
an evaluation circuit for receiving said first and said second signals and manipulating said signals to eliminate a contribution of the diameter of said textile product to said first signal.

13. The apparatus of claim 12, wherein said evaluation circuit comprises a calculator; and
wherein said first and said second signals are mathematically combined to eliminate the contribution of said diameter of said textile product to said first signal.

* * * * *